US 6,207,798 B1

(12) United States Patent
Oliff et al.

(10) Patent No.: US 6,207,798 B1
(45) Date of Patent: *Mar. 27, 2001

(54) MODIFIED $PE_{40}$ TOXIN FUSION PROTEINS

(75) Inventors: Allen I. Oliff, Gwynedd Valley; Gwynneth M. Edwards, Collegeville; Deborah D. Jones, Bala Cynwyd, all of PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/798,447

(22) Filed: Feb. 10, 1997

Related U.S. Application Data

(63) Continuation of application No. 08/632,923, filed on Apr. 16, 1996, now abandoned, which is a continuation of application No. 08/218,451, filed on Mar. 28, 1994, now abandoned, which is a continuation of application No. 08/114,993, filed on Sep. 1, 1993, now abandoned, which is a continuation of application No. 07/803,663, filed on Dec. 2, 1991, now abandoned, which is a continuation of application No. 07/389,092, filed on Aug. 3, 1989, now abandoned.

(51) Int. Cl.[7] .......................... C07K 14/21; A61K 38/45
(52) U.S. Cl. ................. 530/350; 424/183.1; 435/69.1; 435/69.4; 435/69.5; 435/70.1; 514/12; 530/351
(58) Field of Search ................. 424/183.1; 435/69.1, 435/69.4, 69.5, 69.7, 70.1, 71.3; 514/12; 530/350, 351, 387.3, 388.22, 391.7

(56) References Cited

U.S. PATENT DOCUMENTS

| | | | |
|---|---|---|---|
| 4,518,584 | * | 5/1985 | Mark . |
| 4,545,985 | | 10/1985 | Pasten et al. . |
| 4,664,911 | | 5/1987 | Uhr et al. . |
| 4,675,382 | | 6/1987 | Murphy . |
| 4,742,003 | | 5/1988 | Derynck et al. ................ 435/68 |
| 4,892,827 | | 1/1990 | Pastan et al. ................ 435/193 |
| 4,959,314 | * | 9/1990 | Mark et al. . |
| 5,621,078 | * | 4/1997 | Riemen et al. . |
| 5,690,928 | * | 11/1997 | Heimbrook et al. . |

FOREIGN PATENT DOCUMENTS

| | | |
|---|---|---|
| 0 192 811 | 9/1986 | (EP) . |
| 192811 | 9/1986 | (EP) . |
| 0 234 599 | 9/1987 | (EP) . |
| 234599 | 9/1987 | (EP) . |
| 0 261 671 | 3/1988 | (EP) . |
| 59-93093 | 10/1983 | (JP) . |
| WO 88 02401 | 9/1987 | (WO) . |

OTHER PUBLICATIONS

Chaudhary, V K et al "Activity of a recombinant fusion protein between transforming growth factor type α & Pseudomonas toxin." Proc. Natl. Acad Sci. v 84 pp. 4538–4542 (Jul. 1987).*
Hwang et al., Cell 48:129–136 1987, Functional Domains of Pseudomonas exotoxin Identified by Deletion Analysis of the Gene Expressed by *E. Coli.*
Bailon, Biotechnology, pp. 1326–1329 Nov. 1988. Purification and Partial Characterization of an Interleukin 2–Pseudomonas Exotoxin Fusion Protein.
Murphy et al., PNAS USA 83:8258–8262 1986, Genetic construction, expression, and melanoma–selective cytotoxicity of a diphtheria toxin–related alpha–melanocyte–stimulating hormone fusion protein.
Kelly et al., PNAS USA 85:3980–3984 1988, Interleukin 2–diphtheria toxin toxin fusion protein can abolish cell–mediate immunity in vivo.
Allured et al., PNAS USA 83:1320–1324 1986, Sturcture of exotoxin A of *Pseudomonas aeruginosa* at 3.0 Angstrom.
Journal of Biological Chem., vol. 264, No. 24, Aug. 25, 1989, pp. 14256–14261, EMBASE No. 88183894.
Gray, G.L. et al., Cloning, nucleotide sequence, and expression in *Escherichia coli* of the exotoxin A structural gene of *Pseudomonas aeruginosa*, (1984), Proc. Natl. Acad. Sci., USA, Biochemistry, 81, pp. 2645–2649.
Jinno, Y., et al., Domain II Mutants of Pseudomonas Exotoxin Deficient in Translocation, (1989), Jour. of Biol. Chem., 264, No. 27, pp. 15953–15959.
Chaudhary, V.K. et al., Role of domain II of Pseudomonas exotoxin in the secretion of proteins into the periplasm and medium by *Escherichia coli*, (1988), Proc. Nat. Acad. Sci., USA, 85, pp. 2939–2943.
Pastan, I. and FitzGerald, D., Pseudomonas Exotoxin: Chimeric Toxins, (1989), Jour. of Biol. Chem., 264, No. 26, pp. 15157–15160.
Siegall, C.B., et al., Functional Analysis of Domains II, Ib, and III of Pseudomonas Exotoxin, (1989), Jour. of Biol. Chem., 264, No. 24, pp. 14256–14261.

* cited by examiner

Primary Examiner—Anthony C Caputa
Assistant Examiner—Stephen Gucker
(74) Attorney, Agent, or Firm—David A. Muthard; Mark R. Daniel

(57) ABSTRACT

We have modified $PE_{40}$ toxin by removing at least two of its four cysteine amino acid residues and have formed hybrid molecules containing modified $PE_{40}$ linked to a cell recognition protein that can be an antibody, a growth factor, a hormone, a lymphokine, or another polypeptide cell recognition protein for which a specific cellular receptor exists whereby the modified $PE_{40}$ toxin is directed to cell types having receptors for the cell recognition protein linked to the modified $PE_{40}$.

7 Claims, 1 Drawing Sheet

MODIFIED PE$_{40}$ TOXIN FUSION PROTEINS

RELATED APPLICATION

Figure 1:
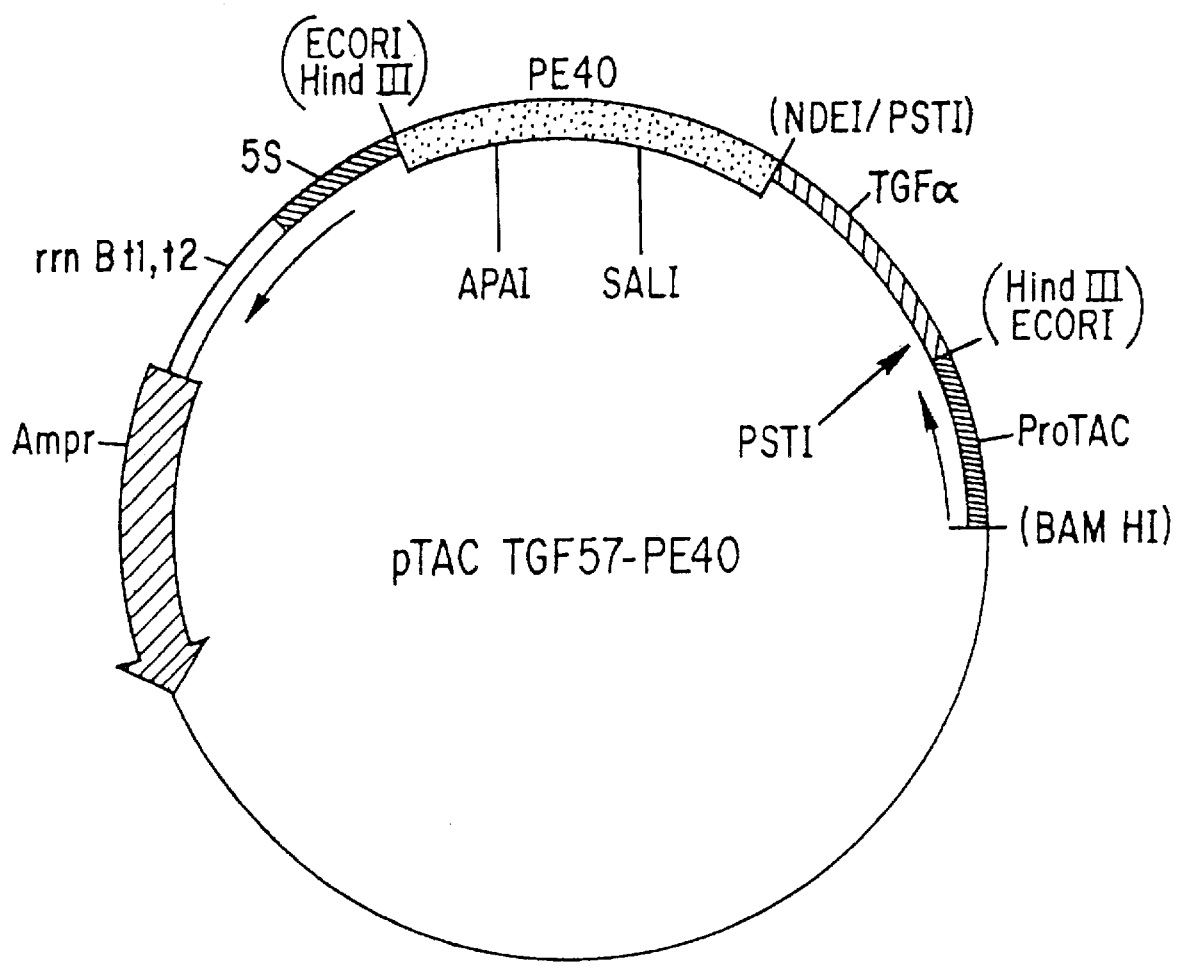

This is a continuation of Ser. No. 08/632,923, filed Apr. 16, 1996, abandoned, which is a continuation of Ser. No. 08/218,451, filed Mar. 28, 1994, abandoned, which is a continuation of Ser. No. 08/114,993, filed Sep. 1, 1993, abandoned, which is a continuation of Ser. No. 07/803,663, filed Dec. 2, 1991, abandoned, which is a continuation of Ser. No. 07/389,092, filed Aug. 3, 1989, abandoned.

BACKGROUND OF THE INVENTION

Traditional cancer chemotherapy relies on the ability of drugs to kill tumor cells in cancer patients. Unfortunately, these same drugs frequently kill normal cells as well as the tumor cells. The extent to which a cancer drug kills tumor cells rather than normal cells is an indication of the compound's degree of selectivity for tumor cells. One method of increasing the tumor cell selectivity of cancer drugs is to deliver drugs preferentially to the tumor cells while avoiding normal cell populations. Another term for the selective delivery of chemotherapeutic agents to specific cell populations is "targeting". Drug targeting to tumor cells can be accomplished in several ways. One method relies on the presence of specific receptor molecules found on the surface of tumor cells. Other molecules, referred to as "targeting agents", can recognize and bind to these cell surface receptors. These "targeting agents" include, e.g., antibodies, growth factors, or hormones. "Targeting agents" which recognize and bind to specific cell surface receptors are said to target the cells which possess those receptors. For example, many tumor cells possess a protein on their surfaces called the epidermal growth factor receptor. Several growth factors including epidermal growth factor (EGF) and transforming growth factor-alpha (TGF-alpha) recognize and bind []to the EGF receptor on tumor cells. EGF and TGF-alpha are therefore "targeting agents" for these tumor cells.

"Targeting agents" by themselves do not kill tumor cells. Other molecules including cellular poisons or toxins can be linked to "targeting agents"to create hybrid molecules that possess both tumor cell targeting and cellular toxin domains. These hybrid molecules function as tumor cell selective poisons by virtue of their abilities to target tumor cells and then kill those cells via their toxin component. Some of the most potent cellular poisons used in constructing these hybrid molecules are bacterial toxins that inhibit protein synthesis in mammalian cells. Pseudomonas exotoxin A is one of these bacterial toxins, and has been used to construct hybrid "targeting-toxin" molecules (U.S. Pat. No. 4,545,985).

Pseudomonas exotoxin A intoxicates mammalian cells by first binding to the cell's surface, then entering the cell cytoplasm and inactivating elongation factor 2 which is a cellular protein required for protein synthesis. Pseudomonas exotoxin A has been used to construct anticancer hybrid molecules using monoclonal antibodies and protein hormones. However, one problem with these hybrid molecules is that they exhibit toxicity towards normal cells. At least part of the toxicity associated with hybrid molecules containing pseudomonas exotoxin A is due to the ability of pseudomonas exotoxin A by itself to bind to and enter many types of mammalian cells. Therefore, hybrid molecules formed between pseudomonas exotoxin A and specific "targeting agents" can bind to many normal cells in addition to the cells recognized by the "targeting agent". One method of dealing with this problem is to modify pseudomonas exotoxin A so that it is no longer capable of binding to normal cells. This can be accomplished by removing that portion of the pseudomonas exotoxin A molecule which is responsible for its cellular binding activity. A truncated form of the pseudomonas exotoxin A molecule has been prepared which retains the ability to inactivate elongation factor 2 but no longer is capable of binding to mammalian cells. This modified pseudomonas exotoxin A molecule is called pseudomonas exotoxin-40 or PE$_{40}$ (Hwang et al., Cell 48: 129–136 1987).

PE$_{40}$ has been linked to several targeting molecules including TGF-alpha (Chaudhary et al., PNAS USA 84: 4583–4542 1987). In the case of TGF-alpha, hybrid molecules containing PE$_{40}$ and TGF-alpha domains are capable of specifically binding to tumor cells that possess EGF receptors and intoxicating these cells via inhibiting protein synthesis. In order for this hybrid molecule to efficiently bind to the EGF receptor it must assume the proper conformation. Efficient receptor binding is also dependent on having the "targeting domain" properly exposed so that it is accessible for binding. When TGF-alpha and PE$_{40}$ hybrid molecules are produced as fusion proteins in bacteria using recombinant DNA techniques the majority of hybrid molecules exhibit poor EGF receptor binding activity.

DISCLOSURE STATEMENT

1. U.S. Pat. No. 4,545,985 teaches that pseudomonas exotoxin A can be conjugated to antibodies or to epidermal growth factor. U.S. Pat. No. 4,545,985 further teaches that these conjugates can be used to kill human tumor cells.
2. U.S. Pat. No. 4,664,911 teaches that antibodies can be conjugated to the A chain or the B chain of ricin which is a toxin obtained from plants. U.S. Pat. No. 4,664,911 further teaches that these conjugates can be used to kill human tumor cells.
3. U.S. Pat. No. 4,675,382 teaches that hormones such as melanocyte stimulating hormone (MSH) can be linked to a portion of the diphtheria toxin protein via peptide bonds. U.S. Pat. No. 4,675,382 further teaches that the genes which encode these proteins can be joined together to direct the synthesis of a hybrid fusion protein using recombinant DNA techniques. This fusion protein has the ability to bind to cells that possess MSH receptors.
4. Murphy et al., PNAS USA 83: 8258–8262 1986, Genetic construction, expression, and melanoma-selective cytotoxicity of a diphtheria toxin-related alpha-melanocyte-stimulating hormone fusion protein. This article teaches that a hybrid fusion protein produced in bacteria using recombinant DNA technology and consisting of a portion of the diphtheria toxin protein joined to alpha-melanocyte-stimulating hormone will bind to and kill human melanoma cells.
5. Kelley et al., PNAS USA 8 5: 3980–3984 1988, Interleukin 2-diphtheria toxin fusion protein can abolish cell-mediated immunity in vivo. This article teaches that a hybrid fusion protein produced in bacteria using recombinant DNA technology and consisting of a portion of the diphtheria toxin protein joined to interleukin 2 functions in nude mice to suppress cell mediated immunity.
6. Allured et al., PNAS USA 83: 1320–1324 1986, Structure of exotoxin A of *Pseudomonas aeruginosa* at 3.0 Angstrom. This article teaches the three dimensional structure of the pseudomonas exotoxin A protein.
7. Hwang et al., Cell 48: 129–136 1987, Functional Domains of Pseudomonas Exotoxin Identified by Deletion Analysis of the Gene Expressed in *E. Coli*. This article teaches that the pseudomonas exotoxin A protein can be divided into three distinct functional domains responsible for: binding to mammalian cells, translocating the toxin protein across lysosomal membranes, and ADP ribosylating elongation factor 2 inside mammalian cells. This article further teaches that these functional domains correspond to distinct regions of the pseudomonas exotoxin A protein.

8. European patent application 0 261 671 published Mar. 30, 1988 teaches that a portion of the pseudomonas exotoxin A protein can be produced which lacks the cellular binding function of the whole pseudomonas exotoxin A protein but possess the translocating and ADP ribosylating functions of the whole pseudomonas exotoxin A protein. The portion of the pseudomonas exotoxin A protein that retains the translocating and ADP ribosylating functions of the whole pseudomonas exotoxin A protein is called pseudomonas exotoxin-40 or PE-40. PE-40 consists of amino acid residues 252–613 of the whole pseudomonas exotoxin A protein as defined in Gray et al., PNAS USA 81: 2645–2649 1984. This patent application further teaches that PE-40 can be linked to transforming growth factor-alpha to form a hybrid fusion protein produced in bacteria using recombinant DNA techniques.
9. Chaudhary et al., PNAS USA 84: 4538–4542 1987, Activity of a recombinant fusion protein between transforming growth factor type alpha and Pseudomonas toxin. This article teaches that hybrid fusion proteins formed between PE-40 and transforming growth factor-alpha and produced in bacteria using recombinant DNA techniques will bind to and kill human tumor cells possessing epidermal growth factor receptors.
10. Bailon, Biotechnology, pp. 1326–1329 November 1988. Purification and Partial Characterization of an Interleukin 2-Pseudomonas Exotoxin Fusion Protein. This article teaches that hybrid fusion proteins formed between PE-40 and interleukin 2 and produced in bacteria using recombinant DNA techniques will bind to and kill human cell lines possessing interleukin 2 receptors.

OBJECTS OF THE INVENTION

It is an object of the present invention to provide modifications of $PE_{40}$ which permit efficient binding of hybrid molecules formed between "targeting agents" and modified $PE_{40}$ molecules to cellular receptors that recognize the "targeting agent". It is another object of this invention to provide a method for recovering the hybrid proteins produced between "targeting agents" and modified $PE_{40}$ as fusion proteins in bacteria. Another object of the present invention is to provide a hybrid (or fusion) protein having a cell receptor binding domain (or region) and a $PE_{40}$ domain (or region) wherein the $PE_{40}$ domain has been modified wherein the hybrid protein to the epidermal growth factor receptor or to the receptor bound by the targeting agent linked to the modified $PE_{40}$ is cytotoxic. Another object is to provide a hybrid protein that is more readily purified. These and other objects of the present invention will be apparent from the following description.

SUMMARY OF INVENTION

The present invention provides a hybrid molecule comprising a modified $PE_{40}$ domain bonded to a protein targeting domain. The modified $PE_{40}$ domain contains other amino acids such as, e.g., alanine substituted for the cysteine residues in $PE_{40}$, or the cysteine residues are deleted. The hybrid molecules of the present invention bind to targeted receptors on human tumor cells.

BRIEF DESCRIPTION OF THE DRAWING

The drawing shows the plasmid of example 2: PTAC TGF57-PE40.

DETAILED DESCRIPTION OF THE INVENTION

Hybrid molecules formed between TGF-alpha and $PE_{40}$ are characterized in three primary assay systems. These assays include: 1—ADP ribosylation of elongation factor 2 which measures the enzymatic activity of TGF-alpha-$PE_{40}$ that inhibits mammalian cell protein synthesis, 2—inhibition of radiolabeled EGF binding to the EGF receptor on membrane vesicles from A431 cells which measures the EGF receptor binding activity of TGF-alpha-$PE_{40}$, and 3—cell proliferation as assessed by conversion of 3-[4,5-dimethylthiazol-2-yl]-2,5-diphenyltetrazolium bromide (MTT) to formazan which is used to measure the survival of tumor cells following exposure to TGF-alpha-$PE_{40}$. These assays are performed as previously described (Dominic et al., Infection and Immunity 16: 832–841 1977, Cohen et al., J. Biol. Chem. 257: 1523–1531 1982, Riemen et al., Peptides 8: 877–885 1987, Mosmann J. Immunol. Methods 65: 55–63 1983).

Briefly, to determine peptide binding to the EGF receptor, A431 membrane vesicles were incubated with radio-iodinated peptide; bound and unbound ligand were then separated by rapid filtration which retained the vesicles and associated radioligand. For most assays, the radioligand was $^{125}$I-EGF obtained from New England Nuclear. For some assays, homogeneous (HPLC) EGF was radio-iodinated using Chloramine T.

EGF binding assays were carried out in a total reaction volume of 100 $\mu$l in Dulbecco's phosphate-buffered saline (pH 7.4) containing 1% (w/v) Pentax Fraction V Bovine Serum Albumin, 1 nM $^{125}$I-EGF (150 $\mu$Ci/$\mu$g), and shed A431 plasma membrane vesicles (35$\mu$ membrane protein). To assess non-specific binding, 100 nM unlabelled EGF or Peak IV was included in the assay. At time 0, the reaction was initiated by the addition of membrane vesicles. After 30 minutes at 37° C., the vesicles were collected on glass fiber filter mats and washed for 20 seconds with Dulbecco's phosphate-buffered saline, using a Skatron Cell Harvester, Model 7000. $^{125}$I-EGF retained by the filters was then quantitated by gamma spectrometry. Assay points were performed in triplicate.

Specifically, to determine cell killing activity, MTT (3-(4,5-dimethylthiazol-2-yl)-2,5-diphenyl tetrazolium bromide; Sigma catalog no. M2128) was dissolved in PBS at 5 mg/ml and filtered to sterilize and remove a small amount of insoluble residue present in some batches of MTT. At the times indicated below, stock MTT solution (10 $\mu$l per 100 $\mu$l medium) was added to all wells of an assay and plates were incubated at 37° C. for 4 h. Acid-isopropanol (100 $\mu$l of 0.04 N NCl in isopropanol) was added to all wells and mixed thoroughly to dissolve the dark blue crystals. After a few minutes at room temperature to ensure that all crystals were dissolved, the plates were read on a Dynatech MR580 Microelisa reader, using a test wavelength of 570 nm, a reference wavelength of 630 nm, and a calibration setting of 1.99 (or 1.00 if the samples were strongly colored). Plates were normally read within 1 h of adding the isopropanol.

To create new TGF-al pha-$PE_{40}$ hybrid molecules we first produced a series of recombinant DNA molecules that encoded either TGF-alpha-$PE_{40}$ or specifically modified versions of TGF-alpha-$PE_{40}$. The original or parental TGF-alpha-$PE_{40}$ gene was molecularly cloned in a bacterial TAC expression plasmid vector (pTAC TGF57-PE40) using distinct segments of cloned DNA as described in Example 2. The pTAC TGF57-PE40 DNA clone was used as the starting reagent for constructing specifically modified versions of TGF-alpha-$PE_{40}$ DNA. The specific modifications of the pTAC TGF57-PE40 DNA involve site specific mutations in the DNA coding sequence required to replace two or four of the cysteine codons within the $PE_{40}$ domain of the pTAC TGF57-PE40 DNA with codons for other amino acids. Alternatively, the site specific mutations can be engineered to delete two or four of the cysteine codons within the PE40 domain of pTAC TGF57-PE40. The site specific mutations in the pTAC TGF57-PE40 DNA were constructed using the methods of Winter et al., Nature 299: 756–758 1982. Specific examples of the mutated pTAC TGF57-PE40 DNAs are presented in Example 3. The amino acid sequence of the hybrid protein encoded by the pTAC TFG57-PE40 DNA is presented in Example 3. The four cysteine residues in the $PE_{40}$ domain of the parental TGF-alpha-$PE_{40}$ hybrid protein are designated residues $Cys^{265}$, $Cys^{287}$, $Cys^{372}$, and $Cys^{379}$ (Example 3). Amino acid residues are numbered as defined in Gray et al, PNAS USA 81: 2645–2649 (1984). The modified TGF-alpha-$PE_{40}$ hybrid proteins generated from the specifically mutated pTAC TGF57-PE40 DNA contain substitutions or deletions of residues [$Cys^{265}$ and $Cys^{287}$] or [$Cys^{372}$ and $Cys^{379}$], or [$Cys^{265}$, $Cys^{287}$, $Cys^{372}$ and $Cys^{379}$]. To simplify the nomenclature for describing the modified hybrid proteins produced from these mutated pTAC TGF57-PE40 DNAs we have designated the amino acid residues at positions 265 and 287 the "A" locus and the residues at positions 372 and 379 the "B" locus. When cysteines are present at amino acid residues 265 and 287 as in parental TGF-alpha-$PE_{40}$ hybrid molecule, the locus is capitalized (i.e. "A"). When the cysteines are substituted with other amino acids such as, for example, alanine, phenylalanine, valine, leucine or isoleucine, or deleted from residues 265 and 287 the locus is represented by a lower case "a". Similarly, if the amino acid residue at positions 372 and 379 are cysteines the locus is represented by an upper case "B" while a lower case "b" represents this locus when the amino acid residues at positions 372 and 379 are substituted with other amino acids or deleted. Thus when all four cysteine residues in the $PE_{40}$ domain of TGF-alpha-$PE_{40}$ are substituted with alanines the modified hybrid protein is designated TGF-alpha-$PE_{40}$ ab. In a similar fashion the parental TGF-alpha-$PE_{40}$ hybrid protein with cysteines at amino acid residue positions 265, 287, 372 and 379 can be designated TGF-alpha-$PE_{40}$ AB.

Both the TGF-alpha-$PE_{40}$ AB hybrid protein and the modified TGF-alpha-$PE_{40}$ hybrid proteins are produced in *E. coli* using the TAC expression vector system described by Linemeyer et al., Bio-Technology 5: 960–965 1987. The recombinant hybrid proteins produced in these bacteria are harvested and purified by lysing the bacteria in guanidine hydrochloride followed by the addition of sodium sulphite and sodium tetrathionate. This reaction mixture is subsequently dialyzed and urea is added to solubilize proteins that have precipitated out of solution. The mixture is next centrifuged to remove insoluble proteins and the recombinant hybrid TGF-alpha-$PE_{40}$ proteins are separated using ion exchange chromatography followed by size exclusion chromatography, followed once again by ion exchange chromatography. The purified TGF-alpha-$PE_{40}$ hybrid proteins are next exposed to reducing agents such as beta-mercaptoethanol in order to permit disulfide bonds to form within the hybrid protein between pairs of cysteine residues. Finally, the refolded hybrid proteins are subjected to size exclusion and ion exchange chromatography to isolate highly pure TGF-alpha-$PE_{40}$ protein. The precise details of this purification scheme are described in Example 2. Once purified and refolded the biologic activity of these hybrid proteins can be characterized using the ADP ribosylation, EGF receptor binding, and cell proliferation assays described above.

An important utility of TGF-alpha-$PE_{40}$ lies in its ability to bind to and kill cells possessing EGF receptors. Many human tumor cells possess EGF receptors and therefore are susceptible to the cell-killing effects of TGF-alpha-$PE_{40}$. Other non-cancerous human cells including keratinocytes possess EGF receptors and are also susceptible to the cell-killing activity of TGF-alpha-$PE_{40}$. Several human diseases are characterized by increased proliferation of keratinocytes including psoriasis and warts.

The following examples illustrate the present invention without, however, limiting the same thereto. All of the enzymatic reactions required for molecular biology manipulations, unless otherwise specified, were carried out as described in Maniatis et al. (1982) In: Molecular Cloning: A Laboratory Manual, Cold Spring Harbor Press.

EXAMPLE 1

Production and Isolation of Recombinant TGF-alpha-$PE_{40}$ Fusion Proteins:

Production of Fusion Protein

Transformed *E. coli* JM-109 cells were cultured in 1 L shake flasks in 500 ml LB-Broth in the presence of 100 μg/ml ampicillin at 37° C. After the A600 spectrophotometric absorbance value reached 0.6, isopropyl B-D-thio-galactopyranoside was added to a final concentration of 1 mM. After 2 hours the cells were harvested by centrifugation.

S-Sulphonation of Fusion Protein

The cells were lysed in 8M guanidine hydrochloride, 50 mM Tris pH 8.0, 1 mM EDTA by stirring at room temperature for 2 hours. The lysis mixture was brought to 0.4 M sodium sulphite and 0.1M sodium tetrathionate by adding solid reagents and the pH was adjusted to 9.0 with 1M NaOH. The reaction was allowed to proceed at room temperature for 16 hours.

Preparation for Chromatography

The protein solution was dialysed against a 10,000 fold excess volume of 1 mM EDTA at 4° C. The mixture was then brought to 6M urea, 50 mM Tris pH 8.0, 50 mM NaCl at room temperature and stirred for 2 hours. Any undissolved material was removed by centrifugation at 32,000×g for 30 minutes.

DEAE F.F. Sepharose Chromatography

The cleared supernatant from the previous step was applied to a 26×40 cm DEAE Fast Flow column (Pharmacia LKB Biotechnology Inc.) equilibrated with 6M urea, 50 mM Tris pH 8.0, 50 mM NaCl at a flow rate of 1 ml/minute. The column was washed with the equilibration buffer until all unadsorbed materials were removed as evidenced by a UV 280 spectrophotometric absorbance below 0.1 in the equilibration buffer as it exits the column. The adsorbed fusion protein was eluted from the column with a 1000 ml 50–350 mM NaCl gradient and then concentrated in a stirred cell Amicon concentrator fitted with a YM-30 membrane.

Sephacryl S-300

The concentrated fusion protein (8 mls) was applied to a 2.6×100 cm Sephacryl S-300 column (Pharmacia LKB Biotechnology Inc.) equilibrated with 6M urea, 50 mM Tris pH 8.0, 50 mM NaCl at a flow rate of 0.25 ml/minute. The column was eluted with additional equilibration buffer and 3 ml fractions collected. Fractions containing TGF-alpha-PE$_{40}$ activity were pooled.

Q-sepharose Chromatography

The pooled fractions from the S-300 column were applied to a 1.6×40 cm Q-sepharose column (Pharmacia LKB Biotechnology, Inc.) equilibrated with 6M urea, 50 mM Tris pH 8.0, 50 mM NaCl at a flow rate of 0.7 ml/minute. The column was washed with the equilibration buffer and then eluted with a 600 ml 50–450 mM NaCl gradient. The fractions containing the TGF-alpha-PE$_{40}$ activity were pooled and then dialysed against 50 mM glycine pH 9.0 and stored at −20° C.

Refolding

A sample of the protein was thawed and diluted to a spectrophotometric absorbance at UV A280=0.1 in 50 mM glycine pH 10.5. Beta-mercaptoethanol was added to give a 4:1 molar ratio over the theoretical number of S-sulphonate groups present in the protein sample. The reaction was allowed to proceed for 16 hours at 4° C. after which time the solution was dialysed against a 10,000 fold excess of physiologically buffered saline and stored at −20° C.

EXAMPLE 2

Construction of Recombinant DNA Clones Containing TGF-alpha-PE$_4$ DNA

The TGF-alpha DNA segment was constructed using three sets of synthetic oligonucleotides as described by Defeo-Jones et al., Molecular and Cellular Biology 8: 2999–3007 1988. This synthetic TGF-alpha gene was cloned into pUC-19. DNA from the pUC-19 clone containing recombinant human TGF-alpha was digested with Sph I and Eco RI. The digestion generated a 2.8 kb DNA fragment containing all of pUC-19 and the 5' portion of TGF-alpha. The 2.8 kb fragment was purified and isolated by gel electrophoresis. An Eco RI to Sph I oligonucleotide cassette was synthesized. This synthetic cassette had the sequence indicated below:

5'-CGGACCTCCTGGCTGCGCATCTAGG-3'3'-
GTACGCCTGGAGGACCGACGCGTAGATCCTTAA-5'

For convenience, this oligonucleotide cassette was named 57. Cassette 57 was annealed and ligated to the TGF-alpha containing 2.8 kb fragment forming a circularized plasmid. Clones which contained the cassette were identified by hybridization to radiolabeled cassette 57 DNA. The presence of human TGF-alpha was confirmed by DNA sequencing. Sequencing also confirmed the presence of a newly introduced Fsp I site at the 3' end of the TGF-alpha sequence. This plasmid, named TGF-alpha-57/pUC-19, was digested with HinD III and Fsp I which generated a 168 bp fragment containing the TGF-alpha gene (TGF-alpha-57). A separate preparation of pUC-19 was digested with HinD III and Eco RI which generated a 2.68 kb pUC-19 vector DNA. The PE$_{40}$ DNA was isolated from plasmid pVC 8 (Chaudhary et al., PNAS USA 84: 4538–4542 1987). pVC 8 was digested using Nde I. A flush end was then generated on this DNA by using the standard conditions of the Klenow reaction (Maniatis, et al., supra, p.113). The flush-ended DNA was then subjected to a second digestion with Eco RI to generate a 1.3 kb Eco RI to Nde I (flush ended) fragment containing PE$_{40}$. The TGF-alpha-57 HinD III to Fsp I fragment (168 bp) was ligated to the 2.68 kb pUC-19 vector. Following overnight incubation, the 1.3 kb EcoRI to Nde I (flush ended) PE$_{40}$ DNA fragment was added to the ligation mixture. This second ligation was allowed to proceed overnight. The ligation reaction product was then used to transform JM 109 cells. Clones containing TGF-alpha-57 PE$_{40}$ in pUC-19 were identified by hybridization to radiolabeled TGF-alpha-57 PE$_{40}$ DNA and the DNA from this clone was isolated. The TGF-alpha-57 PE$_{40}$ was removed from the pUC-19 vector and transferred to a TAC vector system described by Linemeyer et al., Bio-Technology 5: 960–965 1987). The TGF-alpha-57 PE$_{40}$ in pUC-19 was digested with HinD III and Eco RI to generate a 1.5 kb fragment containing TGF-alpha-57 PE$_{40}$. A flush end was generated on this DNA fragment using standard Klenow reaction conditions (Maniatis et al., loc. cit.). The TAC vector was digested with HinD III and Eco RI. A flush end was generated on the digested TAC vector DNA using standard Klenow reaction conditions (Maniatis et al., loc. cit. The 2.7 kb flush ended vector was isolated using gel electrophoresis. The flush ended TGF-alpha-57 PE$_{40}$ fragment was then ligated to the flush ended TAC vector. The plasmid generated by this ligation was used to transform JM 109 cells. Candidate clones containing TGF-alpha-57 PE$_{40}$ were identified by hybridization as indicated above and sequenced. The clone containing the desired construction was named pTAC TGF57-PE$_{40}$. The plasmid generated by these manipulations is depicted in Table 1. The nucleotide sequence of the amino acid codons of the TGF-alpha-PE$_{40}$ fusion protein encoded in the pTAC TGF-57-PE40 DNA are depicted in Table 2. The amino acid sequence encoded by the TGF-57-PE40 gene is shown in Table 3.

EXAMPLE 3

Construction of Modified Versions of Recombinant TGF-alpha-PE$_{40}$ Containing DNA Clones: Substitution of Alanin for Cysteines TGF-alpha-PE$_{40}$ aB:

The clone pTAC TGF57-PE40 was digested with SphI and BamHI and the 750 bp SphI-BamHI fragment (specifying the C-terminal 5 amino acids of TGF-alpha and the N-terminal 243 amino acids of PE$_{40}$) was isolated. M13 mp19 vector DNA was cut with SphI and BamHI and the vector DNA was isolated. The 750 bp SphI-BamHI TGF-alpha-PE$_{40}$ fragment was ligated into the M13 vector DNA overnight at 15° C. Bacterial host cells were transformed with this ligation mixture, candidate clones were isolated and their plasmid DNA was sequenced to insure that these clones contained the proper recombinant DNAs. Single stranded DNA was prepared for mutagenesis.

An oligonucleotide (oligo #132) was synthesized and used in site directed mutagenesis to introduce a HpaI site into the TGF-alpha-PE$_{40}$ DNA at amino acid position 272 of PE$_{40}$:

5' CTGGAGACGTTAACCCGTC 3' (oligo #132)

One consequence of this site directed mutagenesis was the conversion of residue number 272 in PE$_{40}$ from phenylalanine to leucine. The mutagenesis was performed as described by Winter et al., Nature, 299: 756–758 1982.

A candidate clone containing the newly created HpaI site was isolated and sequenced to validate the presence of the mutated genetic sequence. This clone was then cut with SphI and SalI. A 210 bp fragment specifying the C-terminal 5 amino acids of TGF-alpha and the N-terminal 70 amino acids of PE$_{40}$ and containing the newly introduced HpaI site was isolated and subcloned back into the parent pTAC TGF57-PE40 plasmid at the SphI-SalI sites. Bacterial host cells were transformed, a candidate clone was isolated and its plasmid DNA was sequenced to insure that this clone contained the proper recombinant DNA. For convenience this clone was named pTAC TGF57-PE40-132. pTAC TGF57-PE40-132 was digested with SphI and HpaI and a 3.96 Kb DNA fragment was isolated. A synthetic oligonucleotide cassette (oligo #153) spanning the C-terminal 5 amino acids of TGF-alpha and the N-terminal 32 amino acids of PE$_{40}$ and containing SphI and HpaI compatible ends was synthesized and ligated to the digested pTAC TGF57-PE40-132:

with this ligation mixture, candidate clones were isolated and their plasmid DNA was sequenced to insure that these clones contained the proper recombinant DNAs. Single stranded DNA was prepared for mutagenesis.

```
5'    CGGACCTCCTGGCCATGGCCGAAGAGGGCGGCAGCCTGGCCGCGCTGACCGCGCA

3'    GTACGCCTGGAGGACCGGTACCGGCTTCTCCCGCCGTCGGACCGGCGCGACTGGCGCGT

CCAGGCTGCACACCTGCCGCTGGAGACGTT  3'

GGTCCGACGTGTGGACGGCGACCTCTGCAA  5'     (oligo #153)
```

This oligonucleotide cassette incorporated a change in the TGF-alpha-PE$_{40}$ DNA so that the codon specifying cysteine at residue 265 now specified alanine. For convenience this plasmid DNA was called pTAC TGF57-PE40-132,153. Bacterial host cells were transformed with pTAC TGF57-PE40-132,153 DNA. Candidate clones were identified by hybridization, isolated and their plasmid DNA was sequenced to insure that it contained the proper recombinant DNA.

pTAC TGF57-PE40-132,153 DNA was digested with HpaI and SalI and a 3.95 Kb vector DNA was isolated. A synthetic oligonucleotide cassette (oligo #142) spanning amino acid residues 272 to 309 of PE$_{40}$ and containing HpaI and SalI compatible ends was synthesized and ligated to the 3.95 Kb pTAC TGF/PE40 132,153 DNA.

An oligonucleotide (oligo #133) was synthesized and used in site directed mutagenesis to introduce a BsteII site into the TGF-alpha-PE$_{40}$ DNA at amino acid position 369 of PE$_{40}$:

5' GACGTGGTGACCCTGAC 3' (oligo #133)

One consequence of this mutagenesis was the conversion of the serine residue at position 369 of PE$_{40}$ to a threonine.

A DNA clone containing the newly created BsteII site was identified, isolated and sequenced to ensure the presence of the proper recombinant DNA. This clone was next digested with ApaI and SalI restriction enzymes. A 120 bp insert DNA fragment containing the newly created BsteII site was isolated and ligated into pTAC TGF57-PE40 that had also been digested with ApaI and SalI. Bacterial host cells were transformed, and a candidate clone was isolated and

```
5'  AACCCGTCATCGCCAGCCGCGCGGCTGGGAACAACTGGAGCAGGCTGGCTATCCGGTGC

3'  TTGGGCAGTAGCGGTCGGCGCGCCGACCCTTGTTGACCTCGTCCGACCGATAGGCCACG

AGCGGCTGGTCGCCCTCTACCTGGCGGCGCGGCTGTCGTGGAACCAGG  3'

TCGCCGACCAGCGGGAGATGGACCGCCGCGCCGACAGCACCTTGGTCCAGCT  5'  (oligo #142)
```

This oligonucleotide cassette changes the codon specifying cysteine at residue 287 so that this codon now specified alanine. For convenience this mutated plasmid DNA was called pTAC TGF57-PE40-132,153,142. Bacterial host cells were transformed with this plasmid and candidate clones were identified by hybridization. These clones were isolated and their plasmid DNA was sequenced to insure that it contained the proper recombinant DNA. The pTAC TGF57-PE40-132,153,142 plasmid encodes the TGF-alpha-PE$_{40}$ variant with both cysteines at locus "A" replaced by ala-sequenced to insure that the proper recombinant DNA was present. This newly created plasmid DNA was called pTAC TGF57-PE40-133. It was digested with BsteII and ApaI and 2.65 Kb vector DNA fragment was isolated.

A BsteII to ApaI oligonucleotide cassette (oligo #155) was synthesized which spanned the region of TGF-alpha-PE$_{40}$ deleted from the pTAC TGF57-PE40-133 clone digested with BsteII and ApaI restriction enzymes. This cassette also specified the nucleotide sequence for BsteII and ApaI compatible ends.

```
5'  GTGACCCTGACCGCGCCGGTCGCCGCCGGTGAAGCTGCGGGCC  3'

3'  GGACTGGCGCGGCCAGCGGCGGCCACTTCGACGC  5'  (oligo #155)
``` nines. Therefore, following the nomenclature described previously this modified version of TGF-alpha-PE$_{40}$ is called TGF-alpha-PE$_{40}$ aB. The amino acid sequence encoded by the TGF-alpha-PE$_{40}$ aB gene is shown in Table 4.

TGF-alpha-PE$_{40}$ Ab:

The clone pTAC TGF57-PE40 was digested with SphI and BamHI and the 750 bp SphI-BamHI fragment (specifying the C-terminal 5 amino acids of TGF-alpha and the N-terminal 252 amino acids of PE$_{40}$) was isolated. M13 mp19 vector DNA was cut with SphI and BamHI and the vector DNA was isolated. The 750 bp SphI-BamHI TGF-alpha-PE$_{40}$ fragment was ligated into the M13 vector DNA overnight at 15° C. Bacterial host cells were transformed This oligonucleotide cassette changed the codons for cysteines at residues 372 and 379 of PE$_{40}$ to codons specifying alanines. Oligonucleotide cassette #155 was ligated to the 2.65 Kb vector DNA fragment. Bacterial host cells were transformed and candidate clones were isolated and sequenced to insure that the proper recombinant DNA was present. This newly created DNA clone was called pTAC TGF57-PE40-133,155. It encodes the TGF-alpha-PE$_{40}$ variant with both cysteines at locus "B" replaced by alanines. Therefore, following the nomenclature described previously this modified version of TGF-alpha-PE$_{40}$ is called TGF-alpha-PE$_{40}$ Ab. The amino acid sequence encoded by the TGF-alpha-PE$_{40}$ Ab gene is shown in Table 5.

TGF-alpha-PE$_{40}$ ab:

The pTAC-TGF57-PE40-132,153,142 plasmid encoding TGF-alpha-PE$_{40}$ aB was digested with SalI and ApaI and the resultant 3.8 Kb vector DNA fragment was isolated. The pTAC TGF57-PE40-133,155 plasmid encoding TGF-alpha-PE$_{40}$ Ab was also digested with SalI and ApaI and the resultant 140 bp DNA fragment containing the cysteine to alanine changes at amino acid residues 372 and 379 of PE$_{40}$ was isolated. These two DNAs were ligated together and used to transform bacterial host cells. Candidate clones were identified by hybridization with a radiolabeled 140 bp DNA from pTAC TGF57-PE40-133,155. Plasmid DNA from the candidate clones was isolated and sequenced to insure the presence of the proper recombinant DNA. This newly created DNA clone was called pTAC TGF57-PE40-132,153, 142,133,155. This plasmid encodes the TGF-alpha-PE$_{40}$ variant with all four cysteines at loci "A" and "B" replaced by alanines. Therefore, following the nomenclature described previously this modified version of TGF-alpha-PE$_{40}$ is called TGF-alpha-PE$_{40}$ ab. The amino acid sequence encoded by the TGF-alpha-PE$_{40}$ ab gene is shown in Table 6.

EXAMPLE 4

Construction of Modified Versions of Recombinant TGF-alpha-PE$_{40}$ Containing DNA Clones: Selection of Cysteine Residues TGF-alpha-PE$_{40}$ aB, TGF-alpha-PE$_{40}$ Ab, and TGF-alpha-PE$_{40}$ ab can also be constructed by removing the cysteine residues at locus "A" and/or locus "B". Construction of these versions of TGF-alpha-PE$_{40}$ are accomplished identically as described in Example 3 except that: for TGF-alpah-PE$_{40}$ aB oligonucleotide cassette 153 is changed such that the alanine codon intended for position 265 is deleted and oligonucleotide cassette 142 is changed such that the alanine codon intended for position 287 is deleted. For TGF-alpha-PE$_{40}$ Ab oligonucleotide cassette 155 is changed such that the alanine codons intended for residues 372 and 379 are deleted. For TGF-alpha-PE$_{40}$ ab the DNA fragments used to construct this recombinant gene are taken from the TGF-alpha-PE$_{40}$ aB and TGF-alpha-PE$_{40}$ Ab gene described in this example.

EXAMPLE 5

Biologic Activities of TGF-alpha-PE$_{40}$ AB, TGF-alpha-PE$_{40}$ Ab, TGF-alpha-PE$_{40}$ aB, and TGF-alpha-PE$_{40}$ ab Proteins The hybrid fusion proteins TGF-alpha-PE$_{40}$ AB, TGF-alpha-PE$_{40}$ Ab, TGF-alpha-PE$_{40}$ aB, TGF-alpha-PE$_{40}$ ab were expressed in bacterial hosts and isolated as described in Example 1. Each protein was then characterized for its ability to inhibit the binding of radiolabeled epidermal growth factor to the epidermal growth factor receptor on A431 cell membrane vesicles and for its ability to kill A431 cells as measured in MTT cell proliferation assays described previously. The following table summarizes the biologic activites of these proteins:

|  | EPIDERMAL GROWTH FACTOR RECEPTOR BINDING IC$_{50}$ nM | A431 CELL KILLING EC$_{50}$ pM |
|---|---|---|
| TGF-alpha - PE$_{40}$ AB | 346 | 47 |
| TGF-alpha - PE$_{40}$ Ab | 588 | 25 |
| TGF-alpha - PE$_{40}$ aB | 27 | 151 |
| TGF-alpha - PE$_{40}$ ab | 60 | 392 |

EXAMPLE 6

Substitution of Other "Targeting Agents" that Bind to the Epidermal Growth Factor Receptor for the TGF-alpha Domain of TGF-alpha-PE$_{40}$ ab The utility of TGF-alpha-PE$_{40}$ lies in its ability to bind to and kill cells possessing epidermal growth factor receptors. Other "targeting agents" can be used to create hybrid molecules with the modified PE$_{40}$ of the present invention that will bind to EGF receptors. For example, the genes for epidermal growth factor or urogastrone or the Shope fibroma virus growth factor, or the vaccinia virus growth factor can be linked to the gene for PE$_{40}$ and used to direct the synthesis of epidermal growth factor-PE$_{40}$, or urogastrone-PE$_{40}$, or Shope fibroma virus growth factor-PE$_{40}$, or vaccinia virus growth factor-PE$_{40}$ hybrid fusion proteins. However, in each case one or more of the modifications to PE$_{40}$ described herein improves the binding of these other hybrid fusion proteins to cells possessing epidermal growth factor receptors.

EXAMPLE 7

Substitution of Other "Targeting Agents" that Bind to Other Receptors on Mammalian Cells for the TGF-alpha Domain of TGF-alpha-PE$_{40}$.

It is to be understood that this invention is directed to modification of the PE$_{40}$ domain of hybrid fusion proteins between PE$_{40}$ and other "targeting agents" that recognize specific receptors on mammalian cells. For example, fusion proteins formed between proteins and modified PE$_{40}$ of the present invention of the general formula: protein X-PE$_{40}$ where protein X is interleukin-2, or interleukin-3, or interleukin-4, or interleukin-6, or platelet derived growth factor, or any other protein that recognizes and binds to a specific mammalian cell receptor have improved binding properties to their respective cellular receptors.

EXAMPLE 8

Bilogic Activity of TGF-alpha-PE$_{40}$ ab Against Human Keratinocytes

Using the cell proliferation assay of Mossmann, J. Immunol. Methods 65: 55–63 (1983), TGF-alpha-PE$_{40}$ ab readily killed the human keratinocytes used in the assay. The concentration of TGF-alpha-PE$_{40}$ required to kill 50% of the keratinocytes (ED$_{50}$) was 11 nM.

TABLE 2

```
ATGGCTGCAGCAGTGGTGTCCCATTTTAATGACTGCCCAGATTCCCACACTCAGTTCTGCTTCCATGGAACATGCAGG
TTTTTGGTGCAGGAGGACAAGCCGGCATGTGTCTGCCATTCTGGGTACGTTGGTGCGCGCTGTGAGCATGCGGACCTC
CTGGCTGCTATGGCCGAAGAGGGCGGCAGCCTGGCCGCGCTGACCGCGCACCAGGCTTGCCACCTGCCGCTGGAGACT
TTCACCCGTCATCGCCAGCCGCGCGGCTGGGAACAACTGGAGCAGTGCGGCTATCCGGTGCAGCGGCTGGTCGCCCTC
TACCTGGCGGCGCGGCTGTCGTGGAACCAGGTCGACCAGGTGATCCGCAACGCCCTGGCCAGCCCCGGCAGCGGCGGC
GACCTGGGCGAAGCGATCCGCGAGCAGCCGGAGCAGGCCCTGGCCCTGACCCTGGCCGCCGCCGAGAGCGAGCGCTTC
GTCCGGCAGGGCACCGGCAACGACGAGGCCGGCGCGGCCAACGCCGACGTGGTGAGCCTGACCTGCCCGGTCGCCGCC
GGTGAATGCGCGGGCCCGGCGGACAGCGGCGACGCCCTGCTGGAGCGCAACTATCCCACTGGCGCGGAGTTCCTCGGC
GACGGCGGCGACGTCAGCTTCAGCACCCGCGGCACGCAGAACTGGACGGTGGAGCGGCTGCTCCAGGCGCACCGCCAA
CTGGAGGAGCGCGGCTATGTGTTCGTCGGCTACCACGGCACCTTCCTCGAAGCGGCGCAAAGCATCGTCTTCGGCGGG
GTGCGCGCGCGCAGCCAGGACCTCGACGCGATCTGGCGCGGTTTCTATATCGCCGGCGATCCGGCGCTGGCCTACGGC
TACGCCCAGGACCAGGAACCCGACGCACGCGGCCGGATCCGCAACGGTGCCCTGCTGCGGGTCTATGTGCCGCGCTCG
AGCCTGCCGGGCTTCTACCGCACCAGCCTGACCCTGGCCGCGCCGGAGGCGGCGGGCGAGGTCGAACGGCTGATCGGC
CATCCGCTGCCGCTGCGCCTGGACGCCATCACCGGCCCCGAGGAGGAAGGCGGGCGCCTGGAGACCATTCTCGGCTGG
CCGCTGGCCGAGCGCACCGTGGTGATTCCCTCGGCGATCCCCACCGACCCGCGCAACGTCGGCGGCGACCTCGACCCG
TCCAGCATCCCCGACAAGGAACAGGCGATCAGCGCCCTGCCGGACTACGCCAGCCAGCCCGGCAAACCGCCGCGCGAG
GACCTGAAGTAA
```

TABLE 3

TGF-alpha-PE$_{40}$ AMINO ACID SEQUENCE

```
 -4   -3   -2   -1'TGFa¹                 6                                      16
Met  Ala  Ala  Ala'Val  Val  Ser  His  Phe  Asn  Asp  Cys  Pro  Asp  Ser  His  Thr  Gln  Phe  Cys 26                                      36
Phe  His  Gly  Thr  Cys  Arg  Phe  Leu  Val  Gln  Glu  Asp  Lys  Pro  Ala  Cys  Val  Cys  His  Ser

46            TGFa⁵⁰'            'PE²⁵²
Gly  Tyr  Val  Gly  Ala  Arg  Cys  Glu  His  Ala  Asp  Leu  Leu  Ala'Ala  Met  Ala  Glu'Glu  Gly 263                                     273
Gly  Ser  Leu  Ala  Ala  Leu  Thr  Ala  His  Gln  Ala  Cys  His  Leu  Pro  Leu  Glu  Thr  Phe  Thr 283                                     293
Arg  His  Arg  Gln  Pro  Arg  Gly  Trp  Glu  Gln  Leu  Glu  Gln  Cys  Gly  Tyr  Pro  Val  Gln  Arg 303                                     313
Leu  Val  Ala  Leu  Tyr  Leu  Ala  Ala  Arg  Leu  Ser  Trp  Asn  Gln  Val  Asp  Gln  Val  Ile  Arg 323                                     333
Asn  Ala  Leu  Ala  Ser  Pro  Gly  Ser  Gly  Gly  Asp  Leu  Gly  Glu  Ala  Ile  Arg  Glu  Gln  Pro 343                                     353
Glu  Gln  Ala  Arg  Leu  Ala  Leu  Thr  Leu  Ala  Ala  Ala  Glu  Ser  Glu  Arg  Phe  Val  Arg  Gln 363                                     373
Gly  Thr  Gly  Asn  Asp  Glu  Ala  Gly  Ala  Ala  Asn  Ala  Asp  Val  Val  Ser  Leu  Thr  Cys  Pro 383                                     393
Val  Ala  Ala  Gly  Glu  Cys  Ala  Gly  Pro  Ala  Asp  Ser  Gly  Asp  Ala  Leu  Leu  Glu  Arg  Asn 403                                     413
Tyr  Pro  Thr  Gly  Ala  Glu  Phe  Leu  Gly  Asp  Gly  Gly  Asp  Val  Ser  Phe  Ser  Thr  Arg  Gly 423                                     433
Thr  Gln  Asn  Trp  Thr  Val  Glu  Arg  Leu  Leu  Gln  Ala  His  Arg  Gln  Leu  Glu  Glu  Arg  Gly 443                                     453
```

TABLE 3-continued

TGF-alpha-PE$_{40}$ AMINO ACID SEQUENCE

Tyr Val Phe Val Gly Tyr His Gly Thr Phe Leu Glu Ala Ala Gln Ser Ile Val Phe Gly 463                                                                                             473
Gly Val Arg Ala Arg Ser Gln Asp Leu Asp Ala Ile Trp Arg Gly Phe Tyr Ile Ala Gly 483                                                                                             493
Asp Pro Ala Leu Ala Tyr Gly Tyr Ala Gln Asp Gln Glu Pro Asp Ala Arg Gly Arg Ile 503                                                                                             513
Arg Asn Gly Ala Leu Leu Arg Val Tyr Val Pro Arg Ser Ser Leu Pro Gly Phe Tyr Arg 523                                                                                             533
Thr Ser Leu Thr Leu Ala Ala Pro Glu Ala Ala Gly Glu Val Glu Arg Leu Ile Gly His 543                                                                                             553
Pro Leu Pro Leu Arg Leu Asp Ala Ile Thr Gly Pro Glu Glu Glu Gly Gly Arg Leu Glu 563                                                                                             573
Thr Ile Leu Gly Trp Pro Leu Ala Glu Arg Thr Val Val Ile Pro Ser Ala Ile Pro Thr 583                                                                                             593
Asp Pro Arg Asn Val Gly Gly Asp Leu Asp Pro Ser Ser Ile Pro Asp Lys Glu Gln Ala 603                                                                                             613
Ile Ser Ala Leu Pro Asp Tyr Ala Ser Gln Pro Gly Lys Pro Pro Arg Glu Asp Leu Lys

TABLE 4

TGF-alpha-PE$_{40}$-aB AMINO ACID SEQUENCE

-4  -3  -2  -1 'TGFa$^1$                                        6                                                                        16
Met Ala Ala Ala'Val Val Ser His Phe Asn Asp Cys Pro Asp Ser His Thr Gln Phe Cys 26                                                                                               36
Phe His Gly Thr Cys Arg Phe Leu Val Gln Glu Asp Lys Pro Ala Cys Val Cys His Ser

46              TGFa$^{50}$'                  'PE$^{252}$    254
Gly Tyr Val Gly Ala Arg Cys Glu His Ala Asp Leu Leu Ala Met Ala Glu'Glu Gly Gly 264                                                                                              274
Ser Leu Ala Ala Leu Thr Ala His Gln Ala Ala His Leu Pro Leu Glu Thr Leu Thr Arg 284                                                                                              294
His Arg Gln Pro Arg Gly Trp Glu Gln Leu Glu Gln Ala Gly Tyr Pro Val Gln Arg Leu 304                                                                                              314
Val Ala Leu Tyr Leu Ala Ala Arg Leu Ser Trp Asn Gln Val Asp Gln Val Ile Arg Asn 324                                                                                              334
Ala Leu Ala Ser Pro Gly Ser Gly Gly Asp Leu Gly Glu Ala Ile Arg Glu Gln Pro Glu 344                                                                                              354
Gln Ala Arg Leu Ala Leu Thr Leu Ala Ala Ala Glu Ser Glu Arg Phe Val Arg Gln Gly 364                                                                                              374
Thr Gly Asn Asp Glu Ala Gly Ala Ala Asn Ala Asp Val Val Ser Leu Thr Cys Pro Val 384                                                                                              394
Ala Ala Gly Glu Cys Ala Gly Pro Ala Asp Ser Gly Asp Ala Leu Leu Glu Arg Asn Tyr 404                                                                                              414
Pro Thr Glu Ala Glu Phe Leu Gly Asp Gly Gly Asp Val Ser Phe Ser Thr Arg Gly Thr 424                                                                                              434
Gln Asn Trp Thr Val Glu Arg Leu Leu Gln Ala His Arg Gln Leu Glu Glu Arg Gly Tyr 444                                                                                              443
Val Phe Val Gly Tyr His Gly Thr Phe Leu Glu Ala Ala Gln Ser Ile Val Phe Gly Gly 464                                                                                              474
Val Arg Ala Arg Ser Gln Asp Leu Asp Ala Ile Trp Arg Gly Phe Tyr Ile Ala Gly Asp 484                                                                                              494

TABLE 4-continued

TGF-alpha-PE40-aB AMINO ACID SEQUENCE

```
Pro Ala Leu Ala Tyr Gly Tyr Ala Gln Asp Gln Glu Pro Asp Ala Arg Gly Arg Ile Arg
                                      504                                     514
Asn Gly Ala Leu Leu Arg Val Tyr Val Pro Arg Ser Ser Leu Pro Gly Phe Tyr Arg Thr
                                      524                                     534
Ser Leu Thr Leu Ala Ala Pro Glu Ala Ala Gly Glu Val Glu Arg Leu Ile Gly His Prp
                                      544                                     554
Leu Pro Leu Arg Leu Asp Ala Ile Thr Gly Pro Glu Glu Gly Gly Arg Leu Glu Thr
                                      564                                     574
Ile Leu Gly Trp Pro Leu Ala Glu Arg Thr Val Val Ile Pro Ser Ala Ile Pro Thr Asp
                                      584                                     594
Pro Arg Asn Val Gly Gly Asp Leu Asp Pro Ser Ser Ile Pro Asp Lys Glu Gln Ala Ile
                                      604                                     614
Ser Ala Leu Pro Asp Tyr Ala Ser Gln Pro Gly Lys Pro Pro Arg Glu Asp Leu Lys
```

TABLE 5

TGF-alpha-PE40 Ab AMINO ACID SEQUENCE

```
 -4  -3  -2  -1 'TGFa¹                 6                                      16
Met Ala Ala Ala'Val Val Ser His Phe Asn Asp Cys Pro Asp Ser His Thr Gln Phe Cys
                                      26                                      36
Phe His Gly Thr Cys Arg Phe Leu Val Gln Glu Asp Lys Pro Ala Cys Val Cys His Ser
                                      46         TGFa⁵⁰'              'PE²⁵²
Gly Tyr Val Gly Ala Arg Cys Glu His Ala Asp Leu Leu Ala'Met Ala Glu'Glu Gly
                                      263                                     273
Gly Ser Leu Ala Ala Leu Thr Ala His Gln Ala Cys His Leu Pro Leu Glu Thr Phe Thr
                                      283                                     293
Arg His Arg Gln Pro Arg Gly Trp Glu Gln Leu Glu Gln Cys Gly Tyr Pro Val Gln Arg
                                      303                                     313
Leu Val Ala Leu Tyr Leu Ala Ala Arg Leu Ser Trp Asn Gln Val Asp Gln Val Ile Arg
                                      323                                     333
Asn Ala Leu Ala Ser Pro Gly Ser Gly Gly Asp Leu Gly Glu Ala Ile Arg Glu Gln Pro
                                      343                                     353
Glu Gln Ala Arg Leu Ala Leu Thr Leu Ala Ala Ala Glu Ser Glu Arg Phe Val Arg Gln
                                      363                                     373
Gly Thr Gly Asn Asp Glu Ala Gly Ala Ala Asn Ala Asp Val Val Thr Leu Thr Ala Pro
                                      383                                     393
Val Ala Ala Gly Glu Ala Ala Gly Pro Ala Asp Ser Gly Asp Ala Leu Leu Glu Arg Asn
                                      403                                     413
Tyr Pro Thr Gly Ala Glu Phe Leu Gly Asp Gly Gly Asp Val Ser Phe Ser Thr Arg Gly
                                      423                                     433
Thr Gln Asn Trp Thr Val Glu Arg Leu Leu Gln Ala His Arg Gln Leu Glu Glu Arg Gly
                                      443                                     453
Tyr Val Phe Val Gly Tyr His Gly Thr Phe Leu Glu Ala Ala Gln Ser Ile Val Phe Gly
                                      463                                     473
Gly Val Arg Ala Arg Ser Gln Asp Leu Asp Ala Ile Trp Arg Gly Phe Tyr Ile Ala Gly
                                      483                                     493
Asp Pro Ala Leu Ala Tyr Gly Tyr Ala Gln Asp Gln Glu Pro Asp Ala Arg Gly Arg Ile
                                      503                                     513
Arg Asn Gly Ala Leu Leu Arg Val Tyr Val Pro Arg Ser Ser Leu Pro Gly Phe Tyr Arg
                                      523                                     533
```

TABLE 5-continued

TGF-alpha-PE40 Ab AMINO ACID SEQUENCE

Thr Ser Leu Thr Leu Ala Ala Pro Glu Ala Ala Gly Glu Val Glu Arg Leu Ile Gly His 543                                      553
Pro Leu Pro Leu Arg Leu Asp Ala Ile Thr Gly Pro Glu Glu Glu Gly Gly Arg Leu Glu 563                                      573
Thr Ile Leu Gly Trp Pro Leu Ala Glu Arg Thr Val Val Ile Pro Ser Ala Ile Pro Thr 583                                      593
Asp Pro Arg Asn Val Gly Gly Asp Leu Asp Pro Ser Ser Ile Pro Asp Lys Glu Gln Ala 603                                      613
Ile Ser Ala Leu Pro Asp Tyr Ala Ser Gln Pro Gly Lys Pro Pro Arg Glu Asp Leu Lys

TABLE 6

TGF-alpha-PE40 ab AMINO ACID SEQUENCE

-4  -3  -2  -1'TGFa$^1$              6                                            16
Met Ala Ala Ala'Val Val Ser His Phe Asn Asp Cys Pro Asp Ser His Thr Gln Phe Cys 26                                      36
Phe His Gly Thr Cys Arg Phe Leu Val Gln Glu Asp Lys Pro Ala Cys Val Cys His Ser

46          TGFa$^{50}$'      'PE$^{252}$   254
Gly Tyr Val Gly Ala Arg Cys Glu His Ala Asp Leu Leu Ala Met Ala Glu'Glu Gly Gly 264                                      274
Ser Leu Ala Ala Leu Thr Ala His Gln Ala Ala His Leu Pro Leu Glu Thr Leu Thr Arg 284                                      294
His Arg Gln Pro Arg Gly Trp Glu Gln Leu Glu Gln Ala Gly Tyr Pro Val Gln Arg Leu 304                                      314
Val Ala Leu Tyr Leu Ala Ala Arg Leu Ser Trp Asn Gln Val Asp Gln Val Ile Arg Asn 324                                      334
Ala Leu Ala Ser Pro Gly Ser Gly Gly Asp Leu Gly Glu Ala Ile Arg Glu Gln Pro Glu 344                                      354
Gln Ala Arg Leu Ala Leu Thr Leu Ala Ala Ala Glu Ser Glu Arg Phe Val Arg Gln Gly 364                                      374
Thr Gly Asn Asp Glu Ala Gly Ala Ala Asn Ala Asp Val Val Thr Leu Thr Ala Pro Val 384                                      394
Ala Ala Gly Glu Ala Ala Gly Pro Ala Asp Ser Gly Asp Ala Leu Leu Glu Arg Asn Tyr 404                                      414
Pro Thr Gly Ala Glu Phe Leu Gly Asp Gly Gly Asp Val Ser Phe Ser Thr Arg Gly Thr 424                                      434
Gln Asp Trp Thr Val Glu Arg Leu Leu Gln Ala His Arg Gln Leu Glu Glu Arg Gly Tyr 444                                      454
Val Phe Val Gly Tyr His Gly Thr Phe Leu Glu Ala Ala Gln Ser Ile Val Phe Gly Gly 464                                      474
Val Arg Ala Arg Ser Gln Asp Leu Asp Ala Ile Trp Arg Gly Phe Tyr Ile Ala Gly Asp 484                                      494
Pro Ala Leu Ala Tyr Gly Tyr Ala Gln Asp Gln Glu Pro Asp Ala Arg Gly Arg Ile Arg 504                                      514
Asn Gly Ala Leu Leu Arg Val Tyr Val Pro Arg Ser Ser Leu Pro Gly Phe Tyr Arg Thr 524                                      534
Ser Leu Thr Leu Ala Ala Pro Glu Ala Ala Gly Glu Val Glu Arg Leu Ile Gly His Pro 544                                      554
Leu Pro Leu Arg Leu Asp Ala Ile Thr Gly Pro Glu Glu Glu Gly Gly Arg Leu Glu Thr 564                                      574

TABLE 6-continued

| TGF-alpha-$PE_{40}$ ab AMINO ACID SEQUENCE |
| --- |
| Ile Leu Gly Trp Pro Leu Ala Glu Arg Thr Val Val Ile Pro Ser Ala Ile Pro Thr Asp |
| 584 594 |
| Pro Arg Asn Val Gly Gly Asp Leu Asp Pro Ser Ser Ile Pro Asp Lys Glu Gln Ala Ile |
| 604 613 |
| Ser Ala Leu Pro Asp Tyr Ala Ser Gln Pro Gly Lys Pro Pro Arg Glu Asp Leu Lys |

What is claimed is:

1. A hybrid protein comprising a $PE_{40}$ domain and a protein targeting domain that is a growth factor or a hormone, the $PE_{40}$ domain modified by replacement of at least two cysteine residues by the corresponding number of alanine residues.

2. A hybrid protein according to claim 1 wherein two cysteine residues are each replaced by an alanine residue.

3. A hybrid protein according to claim 1 wherein four cysteine residues are each replaced by an alanine residue.

4. A hybrid protein TGFα$PE_{40}$ab wherein all cysteine residues at loci a and b are each replaced by an alanine residue.

5. A hybrid protein TGFα$PE_{40}$aB wherein the cysteine residues at loci a are each replaced by an alanine residue.

6. A hybrid protein TGFα$PE_{40}$Ab wherein the cysteine residues at loci b are each replaced by an alanine residue.

7. A hybrid protein according to claim 1 wherein the targeting domain binds to the epidermal growth factor receptor.

* * * * *